(12) United States Patent
De Munck et al.

(10) Patent No.: US 7,919,551 B2
(45) Date of Patent: Apr. 5, 2011

(54) BRANCHED OLEFIN COMPOSITIONS (75) Inventors: Nicolaas A. De Munck, Barendrecht (NL); Peter J. Ayre, New Milton (GB); Adrian F. Da Costa, Brussels (BE); Edwin Kooke, Ridderkerk (NL)

(73) Assignee: ExxonMobilChemical Patents Inc., Houston, TX (US)

( * ) Notice: Subject to any disclaimer, the term of this patent is extended or adjusted under 35 U.S.C. 154(b) by 591 days.

(21) Appl. No.: 11/817,855

(22) PCT Filed: Apr. 12, 2006

(86) PCT No.: PCT/EP2006/003550
§ 371 (c)(1),
(2), (4) Date: May 16, 2008

(87) PCT Pub. No.: WO2006/108698
PCT Pub. Date: Oct. 19, 2006

(65) Prior Publication Data
US 2008/0293860 A1 Nov. 27, 2008

(30) Foreign Application Priority Data
Apr. 15, 2005 (GB) .................................. 0507626.0

(51) Int. Cl.
*C08G 73/10* (2006.01)
*C08K 5/09* (2006.01)
*C08F 236/12* (2006.01)
*B60C 1/00* (2006.01)

(52) U.S. Cl. .......... 524/323; 524/570; 524/296; 524/297
(58) Field of Classification Search .................. 524/323, 524/570, 296, 297
See application file for complete search history.

(56) References Cited

U.S. PATENT DOCUMENTS

| 6,060,545 A * | 5/2000 | Gilg ............................... 524/199 |
| 2003/0114718 A1* | 6/2003 | Knoop et al. .................. 568/855 |
| 2004/0254393 A1* | 12/2004 | Godwin et al. .................. 560/98 |

OTHER PUBLICATIONS

John Wiley & Sons, "Olefins, Higher," Kirk-Othmer Encyclopedia of Chemical Technology, vol. 17, Nickel and Nickel Alloys to Paint, Fourth Edition (1996), p. 857 (lines 23-31).

* cited by examiner

*Primary Examiner* — William K Cheung
(74) *Attorney, Agent, or Firm* — Leandro Arechederra; Andrew B. Griffis (57) ABSTRACT

Olefin compositions comprising $C_5$ to $C_{13}$ branched chain olefins are stabilised by the addition of 5 to less than 50 ppm by weight of antioxidant. These lower than normal amounts of antioxidant enable improved yields in a hydroformylation reaction using the olefin composition as feedstock and in esterification reactions employing the alcohol produced in the hydroformylation reaction. Consistent lower levels of antioxidant can be achieved by use of a liquid antioxidant and a pump driven dosing system.

34 Claims, 1 Drawing Sheet

Figure 1

BRANCHED OLEFIN COMPOSITIONS

CROSS REFERENCE TO RELATED PATENT APPLICATIONS

This application is a national stage filing of International Patent Cooperation Treaty Application No. PCT/EP2006/003550 filed Apr. 12, 2006, which claims priority from Great Britain Application No. 0507626.0, filed Apr. 15, 2005, the disclosure of which is fully incorporated herein by reference.

FIELD OF THE INVENTION

The present invention relates to improvements in or relating to branched chain olefin oligomers and to the use of the improved oligomers and their derivatives in subsequent reactions.

BACKGROUND OF THE INVENTION

The condensation reaction of an olefin or a mixture of olefins over an acid catalyst to form higher molecular weight products is a widely used commercial process. This type of condensation reaction is referred to herein as an oligomerisation reaction, and the products are low molecular weight oligomers which are formed by the condensation of typically 2, 3 or 4 olefin molecules with each other. As used herein, the term 'oligomerisation' is used to refer to a process for the formation of oligomers. Low molecular weight olefins (such as ethylene, propene, 2-methylpropene, 1-butene and 2-butene, pentenes and hexenes) can be converted by oligomerisation over a solid phosphoric acid catalyst, an acidic ion-exchange resin, a molecular sieve or a zeolite catalyst, to a product which is comprised of oligomers and which is of value as a high-octane gasoline blending stock and as a starting material for the production of chemical intermediates and end-products. Such chemical intermediates and end-products include alcohols, detergents, esters such as plasticiser esters and synthetic lubricants, polymers of unsaturated esters such as acrylic acid. The reactions typically take place in a plurality of tubular or chamber reactors. Sulfated zirconia, liquid phosphoric acid and sulfuric acid are also known catalysts for oligomerisation.

It is well known that olefins, when in contact with oxygen, can form peroxides which can render the olefins explosive. They can also cause discolouration of the olefin and can also lead to gum formation and other fouling of equipment in which the olefin is stored and/or transported. Peroxide formation can be greater if traces of iron or copper are present such as any rust on equipment. It has therefore been standard practice to incorporate antioxidants (sometimes called inhibitors) into branched chain $C_5$ to $C_{13}$ olefin oligomers in order to inhibit the problems caused by peroxide formation. It has not been necessary to do this if the olefin is to be used without storage or is stored and transported under an inert blanket such as a nitrogen blanket.

Typical antioxidants that have been used include phenolic antioxidants such as di-tertiary-butyl hydroxy toluene or butylated hydroxy toluene (BHT). A minimum of 50 to about 150 ppm by wt of the antioxidant has been used, as is shown by commercial specifications for the olefin. We have found however that the use of amounts of antioxidants in this range has a deleterious impact on subsequent reactions in which the olefin or its derivatives are used as starting materials. For example, if the olefin is used as a feedstock for hydroformylation and particularly cobalt catalysed hydroformylation, the yields in the reaction can be relatively low if such an amount of antioxidant is present. Furthermore we have found that if the alcohol obtained in such a hydroformylation reaction is used in an esterification reaction, and in particular a titanium catalysed esterification reaction, then the cycle time for the esterification reaction is relatively long. In addition, if the alcohol is used to esterify an unsaturated acid such as acrylic acid, and the acrylate ester is then polymerised, the presence of the higher amounts of the inhibitor can cause quality inconsistencies in the polymer such as variable molecular weight distribution. This, in turn, can render the polymers unsuitable for their uses such as adhesive components or lubricant viscosity index improvers.

We have now found that adequate stability may be provided to the olefin, and this may be coupled with desirable performance in subsequent reactions in which the olefin or its derivatives is a feedstock, if the antioxidant is present in an amount from 5 to less than 50 wt ppm of the olefin. We have also developed a technique that allows amounts of antioxidant within this range to be incorporated accurately and consistently into the olefin, thus providing olefins of more predictable stability.

SUMMARY OF THE INVENTION

The present invention therefore provides an olefin composition comprising a branched chain olefin having from 5 to 13 carbon atoms and containing from 5 to less than 50 ppm by weight of an antioxidant, based on the weight of olefin.

The invention further provides the use of such an olefin composition as a feedstock for hydroformylation and also the use of alcohols produced in such a hydroformylation reaction as feedstocks for esterification.

DETAILED DESCRIPTION

To facilitate such uses as set forth above, the olefin compositions of the invention are preferably as rich as possible in olefins, and the proportion of $C_5$ to $C_{13}$ branched olefins in the olefin component is typically also high. It will be understood, though, that because of the processes by which branched olefins are produced commercially, the olefin compositions of the invention may contain, in addition to the specified branched chain olefins, linear olefins and possibly also non-olefins such as paraffins. Desirably the total olefin content of the olefin compositions of the invention is at least 80 wt %, more desirably at least 85 wt, % preferably at least 90 wt %, more preferably at least 95 wt % and most preferably at least 99 wt %, with the balance being non-olefins such as paraffins. In the olefin compositions the proportion of $C_5$ to $C_{13}$ branched olefin is desirably at least 70 wt %, more desirably at least 80 wt %, preferably at least 90 wt %, more preferably at least 95 wt % and most preferably at least 98 wt %. Desirably the proportion of linear olefins is no more than 20 wt %, preferably no more than 10 wt %, more preferably no more than 5 wt %, and most preferably no more than 1 wt %.

The main non-olefinic components in olefin oligomer containing streams, including those that are the subject of the invention, are saturates or paraffins. The saturates level in the olefin compositions of the invention (or of the olefin oligomer material—see below) may be analysed with gas chromatography, using a POLT column available from Chrompack, which is a packed column spiked with $AgNO_3$. The olefins are trapped as a complex of the π-electrons from the olefins with the silver ions from the column, allowing the saturates to elute from the column considerably ahead of the more retained olefins. The column may subsequently be heated to more rapidly desorb also the olefins. These will show up in the spectrum at higher retention times compared to the less retained saturates, and the amount of saturates may then be calculated based on normalisation over the entire spectrum. The method is readily calibrated by analysing a suitable mixture prepared from pure components. The method provides a total amount of saturates content as a result, and if it is calibrated on a weight basis, the result is also provided on a weight basis.

The amount of linear olefins in the olefin compositions of the invention (or of the olefin oligomer material) may be determined by for example capillary GC analysis with on-line or in-situ hydrogenation of the feed olefins before they enter the GC column, a technique also known as "hydro-GC". Typically the apparatus is equipped with a hydrogenation catalyst, such as 0.5% Pt on alumina, which may be present in the glass liner of the GC injector. Hydrogen is preferred as the carrier gas. The column itself may be an apolar squalane column, and the detector may be a conventional Flame Ionisation Detector (FID). The linear olefins will then elute from the column as n-paraffins, of which the retention times in the GC spectrum may be readily determined using known starting materials, so that the relevant peaks may be identified. Performing the same GC analysis without hydrogenation allows to identify the levels of the individual n-paraffins in the composition or material before hydrogenation. The level of linear olefins present, may then be determined by substracting the latter from the former. Because very often the original olefin compositions (or material) before hydrogenation contain little or no n-paraffins, then the n-paraffin level determined by this "hydro-GC" technique is typically already a fairly accurate representation of the linear olefin content of the olefin composition (or material) that is analysed. In the case were n-paraffins are present, then the original saturates content may be determined as described above and taken into account by calculation, in order to determine the linear olefin content. Again, the result is typically obtained on a weight basis due to the calibration method.

In the lower carbon number range, such as with hexenes, the number of possible isomers is limited, and the retention times of most of the individual olefin and paraffin isomers may be sufficiently known, so that the content of paraffins and linear olefins in such an olefin composition or olefin oligomer material may be determined by simple capillary GC analysis.

The present invention also provides a process for the production of the olefin composition defined above, which process comprises
  i) oligomerising one or more $C_2$ to $C_6$ olefins to produce a $C_5$ to $C_{13}$ branched chain olefin oligomer
  ii) separating an olefin oligomer material comprising $C_5$ to $C_{13}$ branched chain olefin oligomer from the product of the oligomerisation reaction
  iii) passing the olefin oligomer material to a storage and/or transportation vessel
  iv) providing 5 to less than 50 ppm by weight of an antioxidant to the olefin oligomer material between the separation and the storage and/or transportation vessel, to form the desired olefin composition.

In a further embodiment the present invention provides a hydroformylation process wherein an olefin composition comprising a $C_5$ to $C_{13}$ branched chain olefin is hydroformylated characterised in that the olefin composition contains from 5 to less than 50 ppm by weight of an antioxidant. In a preferment of this embodiment the hydroformylation process is performed using a cobalt catalyst.

In a further embodiment of the present invention the $C_6$ to $C_{14}$ alcohol produced by the hydroformylation of the composition comprising branched chain olefin and containing 5 to less than 50 ppm of an antioxidant and hydrogenation of the product of hydroformylation, is esterified. In a preferment of this embodiment the alcohol is esterified with a polycarboxylic acid and in particular phthalic acid or anhydride, cyclohexane dicarboxylic acid, adipic acid or trimellitic acid or anhydride, to produce esters suitable for use as plasticisers. The low content of antioxidant in the olefin composition has been found to be particularly beneficial when the esterification reaction is performed in the presence of a titanium containing catalyst. The low content of antioxidant has also been found to be beneficial when the alcohol is used to esterify unsaturated acids to produce esters which are subsequently polymerised.

The $C_5$ to $C_{13}$ branched olefins—containing compositions with which the present invention is concerned, are generally obtained by the oligomerisation of lower olefins such as ethylene, propylene and butene or mixtures thereof. Our preferred method for the oligomerisation of such olefins is described in PCT Publication WO 2005/058777. In this method the olefins are oligomerised over a catalyst such as a solid phosphoric acid catalyst, an acidic ion-exchange resin or a zeolite catalyst.

Solid phosphoric acid (SPA) catalysts are typically prepared by combining a phosphoric acid with a support and drying the resulting material. A commonly used catalyst is prepared by mixing kieselguhr with phosphoric acid, extruding the resulting paste, and calcining the extruded material. The activity of a solid phosphoric acid catalyst is related to the amount and the chemical composition of the phosphoric acid which is deposited on the support.

Phosphoric acid consists of a family of acids, which exist in equilibrium with each other and differ from each other in their degree of condensation. The catalysts are generally supported on silica and consist of silicone phosphate crystals coated with various phosphoric acids. These acids include orthophosphoric acid ($H_3PO_4$), gyro-phosphoric acid ($H_4P_2O_7$), triphosphoric acid ($H_5P_3O_{10}$), and polyphosphoric acids, and the precise composition of a given sample of phosphoric acid will be a function of the $P_2O_5$ and water content of the sample. As the water content of the acid decreases, the degree of condensation of the acid increases. Each of the various phosphoric acids has a unique acid strength and accordingly the catalytic activity of a given sample of solid phosphoric acid catalyst will depend on the $P_2O_5/H_2O$ ratio of the phosphoric acid which is deposited on the surface of the crystals.

The activity of a solid phosphoric acid catalyst, and also its rate of deactivation in an oligomerisation process, will be a function of the degree of catalyst hydration. In an olefin oligomerisation process, a properly hydrated solid phosphoric acid catalyst can be used to convert over 95% of the olefins in a feedstock to higher molecular weight oligomers. However, if the catalyst contains too little water, it tends to have a very high acidity, which can lead to rapid deactivation as a consequence of coking. Further hydration of the catalyst serves to reduce its acidity and reduces its tendency toward rapid deactivation through coke formation. On the other hand, excessive hydration of a solid phosphoric acid catalyst can cause a change in the crystal structure, leading to lower density and swelling. This change may cause the catalyst to soften and physically agglomerate and, as a consequence, can create high pressure drops in fixed bed reactors. Accordingly, there is an optimum level of hydration for a solid phosphoric acid catalyst.

During use, a solid phosphoric acid catalyst will develop a degree of hydration which is a function of feedstock composition and reaction conditions. For example, the level of hydration is affected by the water content of the feedstock which is being contacted with the catalyst, and also by the temperature and pressure at which the catalyst is used. The vapour pressure of water over a solid phosphoric acid catalyst varies with temperature and it is important to keep the water content of the feedstock in equilibrium with that of the catalyst with which it is being contacted. If a substantially anhydrous hydrocarbon feedstock is used with a properly hydrated catalyst, the catalyst will typically lose water during use, and will develop a less than optimal degree of hydration. Accordingly, when the water content of a feedstock is inadequate to maintain an optimal level of catalyst hydration, it has been conventional to inject additional water into the feedstock. A study of the effect of water on the performance of solid phosphoric acid catalysts as catalysts for the oligomerisation of propene is set forth in a review article by Cavani et al, Applied Catalysis A: General, 97, pp. 177-1196 (1993).

As well as using solid phosphoric acid catalysts, it is known to use acidic zeolite catalysts for the oligomerisation of olefins. PCT publication WO 93/16020 discloses the use of such zeolites, and also that the selectivity and the conversion of the oligomeristion process can be improved by the addition of small amounts of water to the oligomerisation reaction.

Where a zeolite catalyst is used, it may be any zeolite that is active in alkene oligomerisation reactions. For example, there may be used a catalyst selected from the group consisting of zeolites of the TON structure type (for example, H-ZSM-22, H-ISI-1, H-Theta-1, H-Nu-10, KZ-2), or zeolites of the MTT structure type (for example H-ZSM-23, KZ-1) or zeolites of the MFI structure type (for example, H-ZSM-5) or zeolites of the MEL structure type (for example, H-ZSM-11) or zeolites of the MTW structure type (for example, H-ZSM-12), or zeolites with the EUO structure type (for example, EU-1), or zeolite H-ZSM-57, or any member of the ferrierite structure family. Other examples of suitable catalysts are offretites, H-ZSM-4, H-ZSM-18 or zeolite Beta. Reference is made to 'Synthesis of High-Silica Aluminosilicate Zeolites' by P. A. Jacobs and J. A. Martens (published as volume 33 in the series 'Studies in Surface Science and Catalysis') for a review of the synthesis and properties of the aforementioned zeolites.

Additionally, the catalyst can be a zeolite synthesised without addition of a template, for example, faujasites, zeolite L, mordenites, erionites and chabazites, the structures of which are contained in the 'Atlas of Zeolite Structure Types' by C. Baerlocher, W. M. Meier and D. H. Olson (published by Elsevier on behalf of the Structure Commission of the International Zeolite Association, 5th Revised Edition, 2001). Zeolite catalysts having crystal structures that are essentially the same as the crystal structures of the above-mentioned zeolite catalysts, but differing slightly therefrom in chemical composition, may also be used. Examples include zeolite catalysts obtained by removal of a number of aluminium ions from, or by steaming of, the above-mentioned zeolite catalysts; and zeolite catalysts obtained by the addition of different elements (for example boron, iron and gallium), for example, by impregnation or cation exchange, or by incorporation during the zeolite synthesis.

Mixtures of two or more zeolites e.g. a mixture of ZSM-22 and ZSM-57 or ZSM-22 and ZSM-5 can be used as disclosed in EP 0746538 B1. Or alternatively, upon the surface zeolite of each crystal, a layer of another zeolite can be deposited as disclosed in EP 0808298 B1.

Another type of molecular sieve suitable for the oligomerisation process is SAPO-11, which has unidimensional 10-rings like ZSM-22 and ZSM-23.

The zeolite conveniently has a crystallite size up to 5 µm such as within the range of from 0.05 to 5 µm, for example from 0.05 to 2.0 µm, and typically from 0.1 to 1 µm. An as-synthesized zeolite is advantageously converted to its acid form, for example by acid treatment, e.g. by HCl, or by ammonium ion exchange, and subsequently calcined before use in the process of invention. The calcined materials may be post-treated, such as by steaming. It is also possible to use, as is known in the art, a material in which silicon and aluminium have been replaced in whole or in part by other elements. Silicon may, for example, be replaced by germanium and/or phosphorus; and aluminium more especially by boron, galium, chromium and iron. Materials containing such replacement lattice elements are also generally termed zeolites, and the term is used in this broader sense in this specification. The zeolite might be supported or unsupported, for example in the powder form, or used as an extrudate with an appropriate binder. Where a binder is employed, the binder is conveniently a metal oxide, such as alumina or silica and is present in an amount such that the oligomerisation catalyst contains for example from 1 to 99 wt % of the zeolite, more preferably from 50 to 70 wt %.

Other processes that may be used for the oligomerisation of olefins include the nickel oxide catalysed process for the oligomerisation of butenes, as described in U.S. Pat. No. 6,437,170. According to U.S. Pat. No. 6,437,170, catalysts comprising nickel oxide may be used, as described, for example by O'Connor et al in Catalysis Today, 6, (1990) p 329. Supported nickel oxide catalysts may also be used, and possible support materials are silica, alumina, aluminosilicates, aluminosilicates having a layer structure, and zeolites. Particularly suitable catalysts are precipitation catalysts obtainable by mixing aqueous solutions of nickel salts and of silicates, e.g. of sodium silicate and sodium nitrate, and, where appropriate, of other constituents, such as aluminum salts, e.g. aluminum nitrate, and calcining. In this process particular preference is given to catalysts which essentially consist of $NiO$, $SiO_2$, $TiO_2$ and/or $ZrO_2$, and also where appropriate $Al_2O_3$. A most preferred catalyst comprises, as significant active constituents, from 10 to 70% by weight of nickel oxide, from 5 to 30% by weight of titanium dioxide and/or zirconium dioxide and from 0 to 20% by weight of aluminum oxide, the remainder being silicon dioxide. Details of the preparation of these catalysts is given in U.S. Pat. No. 5,849,972.

Alternatively the olefin oligomers may be obtained by the process described in U.S. Pat. No. 5,994,601 namely an oligomerisation of n-butenes or a co-oligomerisation of n-butenes and isobutene as has been described in Oligomerisation of Better Gasoline, Hydrocarbon Processing, 1992, pages 45 ff by F Nierlich et al. The procedure is generally carried out in the liquid phase and employs e.g. as homogeneous catalysts a system which consists of nickel (II) octoate, ethylaluminum chloride and a free fatty acid (DE C 2855423) or preferably uses one of the numerous known fixed catalysts suspended in the oligomerisation mixture which are based on a nickel and silicon such as those disclosed in DD 160037. The catalysts frequently additionally contain aluminum.

Yet another process which may be used for the production of dimers of butene is described in U.S. Pat. No. 4,476,341 employing a homogeneous catalyst system derived from a nickel compound and an organo aluminum compound. This process is further described in U.S. Pat. Nos. 3,655,810; 4,387,262 and 4316851.

It is preferred that the feedstocks for oligomerisation contain a small amount of water, in particular when using SPA or molecular sieve catalysts. It is known that when an alkene-containing feedstock has a water content of less than 0.05 mol %, the water content may be increased by a variety of means. For example, the feedstock can be passed through a thermostatic water saturator. Since the amount of water required to saturate the alkene feedstock depends upon the temperature of the feedstock, control of the water content can then be effected by appropriate control of the temperature of the feedstock. The water content of the feedstock is preferably at least 0.06 mol %, based on the hydrocarbon content of the feedstock.

In most industrial processes such as those described previously, the refinery feed that is to be used in the oligomerisation reaction will contain impurities such as polar compounds. These impurities would be detrimental to the oligomerisation reaction and are frequently removed prior to the reaction, by for instance a water wash. In oligomerisation the feeds are frequently subject to a first alkaline wash to remove acidic polar species followed by a weakly acidic water wash. The last water wash typically produces a feed stream which is saturated with water at the temperature at which the water wash is performed and, accordingly, can be used to provide the water of hydration required in the reaction.

The activity of the catalyst in relation to the particular feed that is being processed may be controlled by the amount of water present. The requirement for the presence of water varies according to the nature of the catalyst. For example, when using a solid phosphoric acid catalyst, water is required for catalyst activation; whereas when using a zeolite catalyst water may be required to temper catalyst activity. Thus the presence of water and the amount of water present is important in all these circumstances.

Accordingly in the preferred processes for the oligomerisation of olefins a hydrated olefin feed is continuously passed through a bed of oligomerisation catalyst under oligomerisation conditions, wherein the water content of the feed is automatically controlled according to the composition of the feed as is described in PCT Publication WO 2005/058777.

When the catalyst comprises a zeolite catalyst, the temperature of the oligomerisation reaction may be, for example, in the range 110° C. to 310° C. If the catalyst comprises solid phosphoric acid, the temperature of the oligomerisation may be, for example, in the range 150° C. to 300° C.

The invention is particularly concerned with olefin compositions comprising branched chain $C_5$ to $C_{13}$ olefins boiling in the range of 30° to 310° C., preferably 30° to 300° C., more preferably 30° to 250° C., and obtained from propylene and/or butene and/or amylene feedstocks or their mixtures, though ethylene may be present as well. Such branched olefins include hexenes, heptenes, octenes, nonenes and dodecenes. In particular the invention is concerned with the following olefins.

| Products | Distillation Range (° C.) ASTM D1078 | |
|---|---|---|
| | Initial Boiling Point | Dry Point |
| Hexenes | 35 | 72 |
| Heptenes | 88 | 97 |
| Octenes | 114 | 126 |
| Nonenes | 135 | 143 |
| Decenes | 155 | 160 |
| Undecenes | 167 | 178 |
| Propylene tetramers or dodecenes | 175 | 225 |
| Tridecenes | 204 | 213 |

The reaction product produced in the oligomerisation reaction will generally be a mixture of desired olefin oligomers, unreacted olefins, diluent (if any is used), water and other impurities. The components are therefore separated, generally by fractional distillation primarily into the olefin oligomers, the unreacted olefins and, if present, the diluent. The unreacted olefins and diluents may be partly or entirely recycled to the oligomerisation reactor. The olefin oligomers may then be purified and separated as required for use in subsequent reactions. For example the oligomers may contain trace amounts of sulphur which may damage a hydroformylation catalyst. Accordingly, if the olefins are to be used as a feed for hydroformylation, the feed may need to be desulphurised.

We have found that the olefin composition of the invention, as compared to those containing more than 50 ppm of the antioxidant, are giving less cause to fouling problems in the heating and/or cooling systems of such desulphurisation step, in particular when this is performed by adsorption on a fixed bed of nickel containing adsorbent or catalyst.

Similarly the olefin oligomers may contain trace amounts of chlorine which may also be detrimental to hydroformylation catalysts and may need to be removed. If the hydroformylation catalyst is not damaged by sulphur or chlorine, the catalyst in the subsequent hydrogenation step to produce the alcohol derivatives may be damaged by these compounds, and hence sulphur and chlorine are preferably removed, most preferably to very low levels such as 1 ppm or below. Furthermore the olefin oligomers themselves are frequently mixtures of oligomers of different carbon number. For example oligomerisation of a mixture of propylene, butene and amylene can result in a mixture of $C_6$ to $C_{13}$ oligomers and this mixture can then be separated by fractional distillation to obtain the oligomer or oligomer mixtures desired for a particular purpose.

Unless the olefin is to be used immediately at the location where it has been produced it will be necessary to store and/or transport the olefin. It is known that, if olefins are exposed to oxygen, peroxides are formed which are deleterious to the colour and further reactivity of the olefin. Furthermore the peroxides can lead to fouling and the production of deposits in the equipment used for the storage and/or transportation of the olefin or in subsequent processing equipment. It is therefore common practice to add an antioxidant to the olefin and typically solid antioxidants have been included in quantities from minimum 50 to maximum 150 ppm by weight of antioxidant. These levels, however, have an adverse impact on the subsequent reactivity of the olefin and its derivatives. We have now found that if the antioxidant is introduced into the olefin in liquid form, then adequate stability of the olefin may be achieved with antioxidant levels from 5 to less than 50 ppm by weight, and that the olefins with this lower level of antioxidant and their derivatives perform better in subsequent reactions. The antioxidant level in the branched olefin composition is less than 50 ppm by weight, for example from 10 to 40 ppm, such as from 20 to 30 ppm. Ideally the antioxidant level is more than 15 ppm, e.g. about 25 ppm. The weight of antioxidant is based on the weight of olefins in the olefin composition, which may contain linear olefin(s) as well as the required branched chain olefin(s).

We prefer that the antioxidant (sometimes called inhibitor) is a phenolic antioxidant, preferably a substituted phenolic antioxidant. Examples of preferred antioxidants are compounds such as di-tert-butyl hydroxy toluene or "butylated hydroxytoluene" (BHT), or "butylated hydroxy ethylbenzene" (BHEB). Preferred antioxidants are phenolic antioxidants which contain a stable substitute such as an alkyl group in the 4 position. Also preferred are phenolic antioxidants which contain a tertiary butyl group at the 2 and/or the 6 position. Examples of preferred antioxidants include 2,6-ditertiarybutyl-4-methyl-phenol and 2,4-dialkyl, 6-tertiary butyl phenol and mixtures thereof. In particular we prefer to use a liquid antioxidant composition containing 2,4-dimethyl, 6-tertiary butyl phenol. This composition may be a mixture also containing 2,5-dimethyl-6-tertiary butyl phenol and BHT such as Topanol AN available from Chance and Hunt Ltd. We prefer to use mixtures that contain at least 50 wt % of 2,4-dimethyl-6-tertiary butyl phenol. One example of such antioxidant is a mixture comprising 56 wt % of 2,4-dimethyl-6-tertiary butyl phenol, 18 wt % BHT and 15 wt % 2,5-dimethyl-4-tertiary butyl phenol, which is available as Annulex BX from Hodgson Chemicals Limited (now Clariant Life Science Molecules (UK) Ltd.).

It is preferred that the antioxidant be a liquid and be introduced into the olefin oligomer material by means of a dosing pump which introduces the liquid antioxidant into the line connecting the oligomerisation unit to the olefin oligomers storage or transportation vessel.

The peroxide radicals are believed to be formed by dissociation of the olefin to form a hydrocarbon free radical which then reacts with oxygen to form a peroxy radical. This peroxy radical may then react with an olefin to form another free hydrocarbon radical and so on. In addition, the peroxides can react to form acids, aldehydes or ketones. It is believed that the mechanism whereby the antioxidant function is performed, is that the phenolic antioxidant reacts with the peroxy radical to form an inhibitor radical which will then react with another free radical and perform as a scavenging agent. The oxygen that causes the oxidation problems can be derived from unblanketed operations, leaks in vacuum systems, air dissolved in water etc.

In a preferred embodiment of the invention, a system for automatically dosing the antioxidant into the olefin oligomer material is provided. The system is preferably provided at a position in the manufacturing process so that the antioxidant is provided shortly after the completion of oligomerisation, and as the olefin oligomer material passes to the storage and/or transportation vessel. The dosing system preferably comprises a metering pump such as a positive displacement, single-acting, reciprocating pneumatic metering pump. These pumps consist of a plunger of selected diameter which reciprocates with a given stroke within a mating cylinder. The volume of antioxidant is therefore accurately controlled by selection of the plunger and cylinder dimensions and varying the stroke length and the number of stroke cycles per minute which may be controlled by means of a Process Flow Tracking Controller.

Accordingly, in operation, the flow of the stream of a particular oligomers product may be measured by a flow meter and the result of this measurement may be relayed to the Process Flow Tracking Controller which determines the amount of antioxidant required and activates the pump accordingly.

In a process in which the oligomerisation reaction produces more than one olefin oligomer and in which the oligomers are separated into different product streams, it is preferred that antioxidant be introduced separately into the individual oligomers streams after separation. In this way the amount of antioxidant can be controlled to match the needs of the final product stream.

It is also preferred that samples of the olefin oligomers are taken regularly from the storage and/or transportation vessel and analysed using a convenient method, such as by gas chromatography or HPLC as explained below to determine the level of antioxidant in the product. If necessary the dosing system may be adjusted according to the results of the analysis.

The antioxidant content of the olefin is conveniently determined by HPLC (High Performance Liquid Chromatography). We prefer to use a Waters 2695 separation module, equipped with a Nova-Pak C18 60 Angstrom 4 micrometer (3.9×150 mm) column and a Photodiode Array Detector. We prefer to use 278 nm as the testing wavelength, where most typical antioxidants give a convenient reading. The mobile phase and operating procedure may be adapted to the nature of the antioxidant that is being used. As procedure, either an isocratic run or a gradient run may be used. For many of the typical antioxidants we prefer to use a gradient run with a flow rate of 1 ml/min and as mobile phase an 80/20 or 90/10 vol % methanol/water mixture for the first 2.5 minutes at the start of the run and the last 3 minutes at the end of the run, separated by a 100% methanol mobile phase for the 12.5 minutes middle section of the run. Isocratic runs we prefer to perform with 100% methanol as mobile phase at a flow rate of 2 ml/min for the full run. Quantification may conveniently be done in reference to an external standard that is prepared and analysed separately. A gradient run will typically provide a better peak separation.

In one embodiment, the olefin oligomers are those produced by the conversion of a mixture of $C_3$ and $C_4$ olefins to produce gasoline blending stock. In such an embodiment, the feedstock will be comprised of at least about 25% by volume of olefins. A typical olefin-containing feedstock to a polymerisation unit for conversion to oligomers in the gasoline boiling range may comprise a mixture of propane, butane, 2-methylpropane, propene, 1-butene, 2-butene and 2-methylpropene, wherein the olefin concentration is in the range from about 35 to about 95 vol %. Ethylene and ethane may also be present, albeit typically in minor amounts. However it will be appreciated that the olefin-containing feedstock can have a variety of other compositions which include but are not limited to, other olefins or olefin mixtures, other diluents and the presence of a minor amount of aromatic compounds. In addition olefin concentrations can be used which are outside this range.

In a further embodiment the present invention provides $C_5$ to $C_{13}$ olefins which are oligomers of ethylene, propylene, butenes and amylenes which can be used as feeds for hydroformylation reactions for the production of aldehydes and alcohols. The aldehydes may be oxidised to produce acids or hydrogenated to produce alcohols. The alcohols may then be used in the production of synthetic esters such as plasticiser esters or synthetic lubricants or in the production of surfactants. The olefins may be hydroformylated by, for example, the processes described in PCT Publication WO 2005/058787. It is preferred to use high pressure hydroformylation technology which is typically cobalt catalysed, but rhodium may also be used as the catalyst. The olefin oligomers of the present invention are particularly useful as feedstocks which are hydroformylated in the manner described in PCT Publication WO 2005/058787 where the low level of antioxidant enables improved hydroformylation reactions. Where the aldehydes produced by this method are hydrogenated, this may readily be accomplished by the method described in PCT Publication WO 2005/058782.

As well as the addition of the antioxidant according to the present invention it may be useful to add other process chemicals to the olefin oligomers containing streams. For example it may be useful to add a corrosion inhibitor such as an amine based corrosion inhibitor to reduce equipment corrosion due to any acids that may be formed. Typically amounts of up to 100 ppm by weight based on the weight of the olefin may be used, particularly 10 to 80 ppm. It is preferred that the corrosion inhibitor be injected into the stabiliser tower employed between the oligomerisation reaction and the product separation system. It may also be useful to add fouling inhibitors particularly to reduce fouling due to the formation of polymer deposits in the equipment that is used to remove undesirable heavy components. Here amounts of up to 100 ppm by weight of materials in the equipment may be used, particularly 10 to 80 ppm. As with the antioxidant, these corrosion and fouling inhibitors may be introduced as a liquid, and by means of a dosing pump.

We have found that it is particularly beneficial to inject such antifoulant in the oligomerisation reactor product upstream of the stabiliser tower. Such antifoulants typically are dispersants that keep preferably both organic and inorganic materials from sticking together. We prefer to use Nalco Antifoulant EC3043A. We have found that, when the antifoulant is injected, the bottom pumps of the downstream tower that takes the C9 olefins overhead, require much less frequent cleaning. Also some of the other towers benefit from the antifoulant injection, by needing less cleaning in their bottom or overhead system.

The olefin oligomers may also be used a feedstocks for alkylation, or they may be used as gasoline components or they may be hydrogenated to produce paraffinic solvents.

Figure 1:
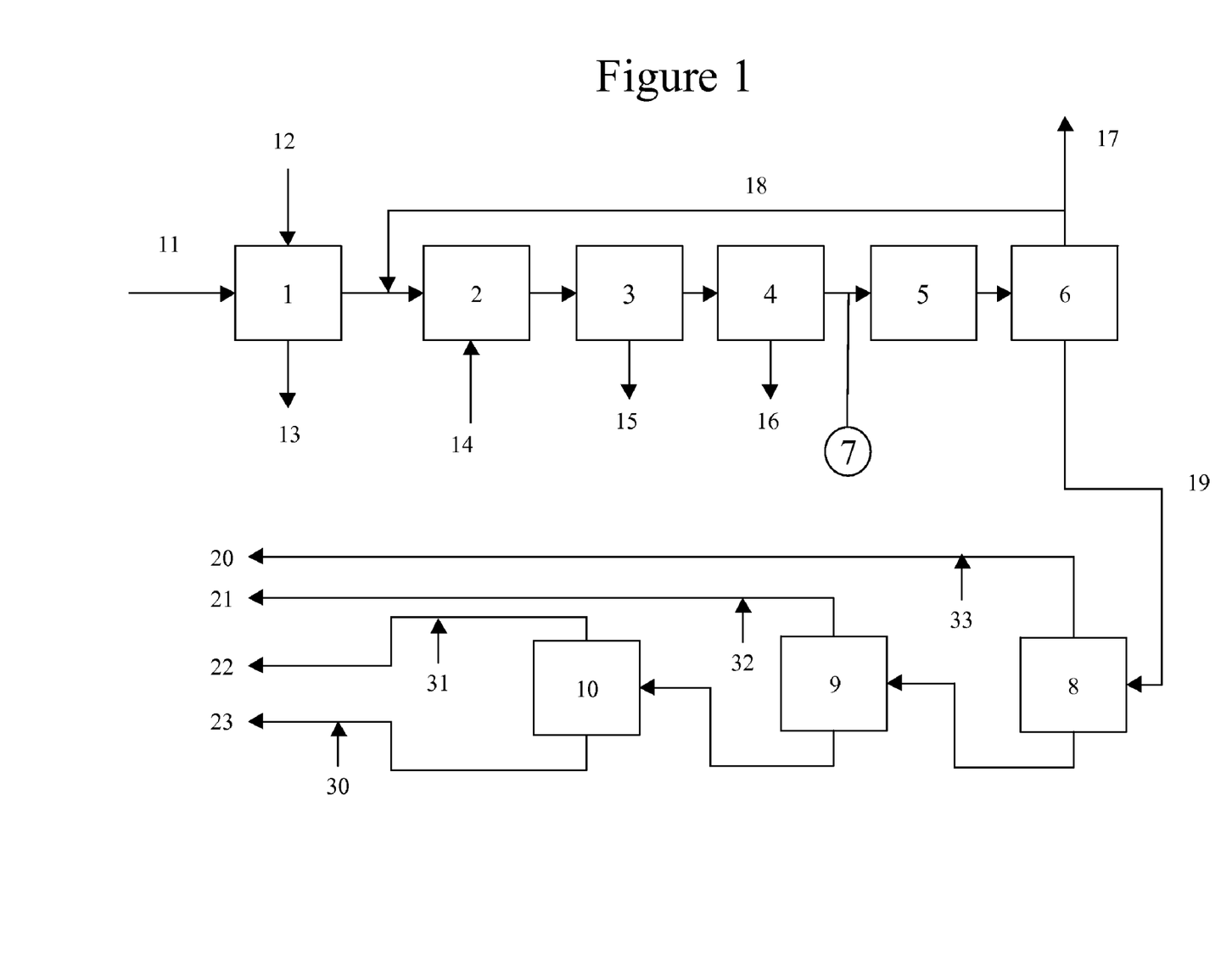
FIG. 1 illustrates schematically an embodiment of the invention.

The operation of the present invention in relation to the oligomerisation of olefins is illustrated by the accompanying FIG. 1, in which (1) denotes an alkaline wash drum or tower to which olefin feed (11) is fed, as is fresh caustic (12). Spent caustic (13) is removed from the alkaline wash operation. The product of the alkaline wash is then typically brought to the desired temperature and sent to a water wash (which may be mildly acidic) at (2), where water (14) is introduced. The olefin stream containing water then passes to a settling drum (3) where water (15) separates out. Part of this water may be recycled to the water wash (2). The olefin stream then passes to a coalescer (4) where also the finer droplets of water (16) are removed and then to the reactor (5). An on line analyser (7) is provided to determine the feed composition and send a signal to alter the hydration level as required, preferably by altering the temperature of the water wash performed at (2). After the oligomerisation reaction in reactor (5), the product passes to stabiliser tower (6) where olefin oligomer is separated as bottoms products (19) and the volatiles removed overhead as (17). These volatiles may be condensed and partially recycled as shown at (18). The oligomers product stream (19) which is typically a mixture of various oligomers then passes to a separation system which may comprise a number of product separation distillation towers, of which three are shown (8), (9) and (10). The product (20) from the top of the tower (8) is the lightest oligomers, the product from the bottom of the tower (8) passes to tower (9) where product (21) is removed from the top of the tower (9). The product from the bottom of the tower (9) passes to tower (10) where it is separated into top product (22) and bottom product (23). As shown, antioxidant is introduced into stream (20) at point (33); into stream (21) and point (32); into stream (22) and point (31) and into stream (23) and point (30). If required, corrosion inhibitor may be introduced into tower (6) and, if required, a fouling inhibitor may be introduced into tower (10), but preferably in the feed to the stabiliser tower (6).

In a further embodiment, the operation of the distillation towers is controlled by on line gas chromatographic analysis such as on lines (20), (21), (22) and (23). In addition it is possible to adjust the olefin composition of the feed to enhance the yield of a particular oligomer by on line determination of product carbon number and/or density and using that information to adjust the balance of the feed composition. We have found this to be particularly useful to enhance the yield of higher oligomers such as nonenes and dodecenes by adjusting the pentene content of the feed according to the density of the stream such as that exiting tower (10) so reducing the formation of less desirable materials such as decene and undecene. In a preferred embodiment of the invention, when primarily propylene is oligomerised to nonene and dodecene, the production of octenes may be significantly increased by adding pentenes to the oligomerisation feed.

The present invention is particularly useful when the olefins are to be hydroformylated to produce aldehydes followed by hydrogenation to produce alcohols. It is particularly applicable to the production of $C_6$ to $C_{13}$ alcohols from $C_5$ to $C_{12}$ olefins or olefin mixtures, preferably of $C_7$ to $C_{13}$ alcohols from $C_6$ to $C_{12}$ olefins or olefin mixtures. By way of example, the invention is useful in the production of isoheptyl, isooctyl, isononyl, isodecyl, isotridecyl alcohol each from its respective branched olefin. The invention is especially useful in the production of $C_8$ to $C_{19}$ alcohols from $C_7$ to $C_9$ olefins or olefin mixtures. In the preferred embodiment with the higher octene production, the invention is particularly useful in the production of isononyl alcohols.

The hydroformylation is usually performed at elevated temperatures and pressures using a cobalt or a rhodium catalyst and in order to achieve optimum performance in the hydrogenation section it is desirable to remove the cobalt or rhodium species from the product of hydroformylation prior to hydrogenation. When using cobalt, it is preferred that the cobalt level be below 5 ppm by weight, more preferably below 2 ppm during hydrogenation. Accordingly in a further preferment the product of hydroformylation is treated to remove cobalt species so that the cobalt content is below 1 ppm prior to hydrogenation. When using rhodium, it is preferred that the rhodium level be below 0.1 ppm by weight, more preferably below 50 ppb, even more preferably below 10 ppb, most preferably below 5 ppb by weight.

The hydroformylation reaction may be performed at elevated temperature and pressure in the presence of a hydroformylation catalyst. The optimum temperature and pressure will depend upon the selection and dosing of the catalyst, the nature of the olefin feed, both in terms of the carbon number(s) of the olefins, the structure of the olefin (extent of branching and location of double bond) and the concentration of the olefin in the feed which is typically a mixture of saturated and unsaturated (predominately olefinic) materials. Typical pressures for the high pressure process are from 50 to 350 barg, preferably 150 to 350 barg, most preferably from 275 to 325 barg. Typical temperatures range from 120 to 190° C., preferably from 165 or 170 to 188° C., e.g. 165 to 185° C., more preferably from 170 to 185° C., e.g. 170 to 180° C., although certain olefin feeds may preferably be hydroformylated at lower temperatures such as from 100 or 120 to 140° C., typically for reasons of olefin reactivity or reaction selectivity. The catalyst used in the high pressure hydroformylation is usually a cobalt or a rhodium catalyst and generally the active cobalt catalyst is hydr(id)ocobalt(tri- or tetra-)carbonyl and cobalt concentrations of up to 0.8 wt % cobalt on the olefin content of the feed are used, preferably from 0.01 or 0.1 wt % to 0.5 wt % cobalt. Using rhodium under such high pressures, much lower concentrations may be used, such as 0.1 to 200 ppm by weight relative to the olefin feed, preferably 0.2 to 50 ppm, more preferably 0.3 to 20 ppm, even more preferably 0.4 to 5 ppm by weight. Also the temperatures may be lower when using rhodium, using the benefit of its higher activity compared to cobalt, and may be 10, 20, 30 or even 40 degrees C. lower than those when using cobalt.

The hydroformylation catalyst for the high pressure process may be supplied already absorbed in the olefin feed and/or as fresh catalyst. It is preferably supplied absorbed in the olefin feed. In the case of cobalt, the initial cobalt species can be dicobalt octacarbonyl $CO_2(CO)_8$, a salt of cobalt with an acid, e.g. cobalt sulfate or carbonate, and preferably with an organic acid, like formic acid or acetic acid, but also salts with higher molecular weight acids like oleic, stearic, or naphthenic acids are known. It can also be cobalt oxide or hydroxide. This cobalt source may be preformed in a separate reactor in order to convert it to the carbonyl form, or this conversion may occur in the hydroformylation reactor itself. Under the hydroformylation conditions, an equilibrium is believed to exist between two cobaltcarbonyls:

$$2HCo(CO)_4 \leftrightarrows Co_2(CO)_8 + H_2$$

Hydr(id)ocobalt(tetra)carbonyl ($HCo(CO)_4$) is generally believed to be the active catalyst form or at least the precursor to the active catalyst form, which also may be $HCo(CO)_3$. The higher the hydrogen partial pressure in the hydroformylation reaction and the higher the temperature, the greater the concentration of hydrocobalt carbonyl, and hence the greater the reaction rate.

The hydroformylation reaction is exothermal and the reaction is typically fast. The heat given off and the rate of heat release to some extent depend upon the nature and structure of the olefin that is being subject to hydroformylation. In general the less branched the olefin the more reactive it tends to be and with branched olefins the reactivity depends on the location of the double bond in relation to the branches. Olefins in which the double bond is located between two branches have, for example, a low reactivity.

It is therefore important that the conditions of the hydroformylation reaction are controlled to minimise fluctuations in the reaction temperature which can cause variations in the product formed and plating out of cobalt metal from the catalyst when using the preferred cobalt catalysed hydroformylation. Control is also important for safety purposes to prevent reaction runaway. Accordingly, in addition to optimizing gas utilization, careful management of the gas profile according to PCT Publication WO 2005/058787 helps to optimize the reaction temperature, with the beneficial effects of increasing reaction yield and minimising or eliminating the plating out of the cobalt within the reactor, which can occur if the reaction temperature is too high. In this case, extensive cleaning is required with for example nitric acid, requiring that the reactor be taken out of service.

In a preferred aspect of the present invention, hydroformylation takes place in a series of reactors and the composition of the materials fed to the second and any subsequent hydroformylation reactors is controlled by recycle of product gasses according to PCT Publication WO 2005/058787. Use of this preferred technology aids control of the gas compositions and the temperatures that are created in the reactors. These techniques therefore lead to higher conversion, higher yields and higher selectivity under constant and safe conditions.

When using a cobalt catalyst, the molar ratio of hydrogen to carbon monoxide in the fresh syngas is typically about 1.3:1 since at this ratio the plating out of the cobalt is substantially avoided, or sufficiently low to be acceptable. However, when using a series of reactors for hydroformylation, due to the reaction in the first reactor where there is some conversion of olefins to aldehydes and alcohols, there will be a change in the ratio of hydrogen to carbon monoxide. This change will depend on the degree of conversion to alcohol or aldehyde since the conversion to alcohol requires twice as much hydrogen as is used in the formation of an aldehyde. Accordingly, it may be necessary to replenish the hydrogen level in the second and perhaps subsequent reactors (if used) and this can be accomplished by balancing the composition of the recycle gasses and/or by introducing unreacted gasses from the downstream hydrogenation reactor used to convert aldehydes in the final product of hydroformylation into alcohols. Such recycle is described in our above-mentioned copending patent application.

Ideal syngas compositions, expressed as mole ratio of hydrogen to carbon monoxide, are not always available. For example, where the ideal composition may be at a 1.3 ratio, the gas may have a higher hydrogen content such as a ratio of 1.5. As hydrogen and carbon monoxide are reacted away from this gas in roughly equal portions in the initial stages of the hydroformylation (Oxo) reaction, the hydrogen to CO ratio will continue to increase. In such a case, the minimum partial pressure requirements for CO, needed to provide stability of the catalyst complex, are met by using more excess fresh gas and avoiding the recycle of any gas containing less CO than the minimum requirement. The reactor operating temperature may also be reduced to compensate for the higher reactivity and the higher propensity for cobalt carbonyl to become unstable.

Syngas may be available at a composition less rich in hydrogen than desired, say at a ratio of 0.8. In this case, economy of syngas utilization is achieved by recycling hydrogen depleted gas from downstream stages and supplementing it with hydrogen, from an external source, to various stages of the hydroformylation reactor sequence, as described in our above-mentioned copending patent application.

In a preferred embodiment to ensure high olefin conversion, the reaction system comprises a series of at least three hydroformylation reactors and, for the reasons discussed above in relation to the second reactor, it is preferred that a hydrogen rich gas, composed of optionally fresh syngas and recycle gas from the hydroformylation reaction and/or from the downstream hydrogenation section, is fed to the third reactor together with the reaction product from the second reactor.

In a further preferred embodiment the reactor system includes a fourth reactor in which the final, say up to 5% conversion of the olefin takes place. In other embodiments, there may be up to 6 reactors. Optionally, part of the recycle gasses and/or a gas rich in hydrogen may be added to the feed of the fourth and/or subsequent reactors.

The hydroformylation reactors are continuous reactors which are preferably gas-lift reactors and, more preferably are loop reactors such as those described in U.S. Pat. No. 4,320,237, U.S. Pat. No. 3,830,846, WO 01/14297, GB 1,308,206 and U.S. Pat. No. 4,312,837 and WO 94/129018. The preferred reactors and their design and operation are described in PCT Publication WO 2005/058787.

The effective operation of the hydroformylation reaction therefore depends upon optimizing the combination of physical conditions such as temperatures, pressures, feed rates of raw materials, space velocity in the reactors and the chemical process conditions. The chemical conditions include in each of the reactors the composition of the olefin feed, relative proportions of olefin feed and other gasses including hydrogen, carbon monoxide and inerts such as nitrogen, methane and carbon dioxide as well as catalyst concentration. The amount of offgas that should be recycled and the amount of syngas and olefin that should be fed to the second and, optionally, subsequent reactors depends on many of these variables. However by establishing the offgas pressure from the high pressure separator and monitoring the composition of the offgas, which includes hydrogen, carbon monoxide and the various inerts, the hydrogen and carbon monoxide partial pressures at the end of the hydroformylation reaction can be calculated and used to control the gas compositions in the upstream hydroformylation reactors. High hydrogen and carbon monoxide partial pressures enhance the stability of the cobalt catalyst, and high hydrogen partial pressures assure a favorable hydroformylation reaction rate. These desires are in conflict with the desire for a higher level of inert buildup, which enables more effective gas purging and improved overall gas utilization, because less valuable hydrogen and carbon monoxide need to be purged with the inerts. This must however be balanced with the constraints imposed by a fixed equipment design pressure, which can result in a lower hydrogen and carbon monoxide content of the high pressure offgas and hence also in hydroformylation. The optimal control point therefore is a compromise between these counteracting preferences. Since the consumption of hydrogen in hydroformylation is greater than the consumption of carbon monoxide, where a series of hydroformylation reactors is used, hydrogen will be depleted relative to carbon monoxide in the first reactor. This difficulty can be overcome by increasing the proportion of hydrogen in the recycle gas that is fed to the second and/or a subsequent hydroformylation reactor.

As a general guide we have found that the pressure at the end of the hydroformylation reaction is ideally kept above 170 barg, preferably above 190 or 200 barg, more preferably above 210 or 220 barg, most preferably above 240 barg in order to avoid cobalt plating in the hydroformylation reactors. We have also found that the carbon monoxide content of the offgas from the high pressure separator is ideally such that the partial pressure of CO is above 75 barg, better above 77 barg, preferably above 84 barg, since, if the partial pressure drops below these levels, cobalt plating may occur in the hydroformylation reactors. Similarly the hydrogen content of the offgas from the high pressure separator is ideally such that the partial pressure of hydrogen is above 75 barg, better above 77 barg, preferably above 84 and more preferably above 91 barg, since, if the partial pressure drops below this level, there is a drop in reaction rate. These issues may be controlled by checking the syngas composition, the pressure drop across the hydroformylation reaction and the proportion of inerts in the various streams, and making the appropriate adjustments. The use of at least two reactors in series and the separate adjustment of the feeds to the reactors by the recycle of gasses can make a significant contribution to the efficiency and effective operation of the hydroformylation reaction as is shown in PCT Publication WO 2005/058787.

In order to improve the selectivity of the hydroformylation reaction, water may be present in the hydroformylation reactors. We have found that the injection of water reduces the formation of formate esters and heavy by-products. When used, water should be injected into the first reactor, and may also be injected into the second and subsequent reactors, if they are used, but we have found that this is not always essential. In a gas-lift reactor, the formation of a significant volume of a stagnant free water phase in the bottom can become an impediment or even an obstruction to the circulation of the reactor fluid. Gas-lift reactors from which any free water is continuously removed from the bottom have been described in WO 01/14297. If there is no water removal capability, the quantity of water that is introduced should preferably not exceed, or not exceed by more than 10 or 20%, the solubility of the water in the reaction mixture, to avoid the formation of a stagnant free water phase in the reactor. We have found that preferably no more than 2 wt % of water, based on the weight of olefin feed, should be used in the first reactor and typically from 1.0 wt % to 1.75 wt %, particularly 1.5 wt % should be used. The weight of the olefin feed is the weight of unsaturated materials in the feed, which is typically above 95 wt % of the feed and frequently about 99 wt % of the feed. Where water is injected into the second reactor, similar considerations may apply depending on the design of the reactor. Due to the different liquid composition in the second reactor, the water solubility may be different in this reactor, typically being higher, and we prefer to use typically a total of 2.5 wt % water present based on the olefin feed. It needs to be understood that these water levels depend on the olefin type and alcohol product that is processed, due to the different water solubility of the corresponding process streams. It also needs to be understood that the distribution among the reactor stages, of the water that is injected, depends on the size of the individual reactor stages.

We have found that the injection of water provides a significant improvement in plant utilization as well as carbon monoxide utilization. The water should be injected in a manner that ensures good mixing of the water with the reactants and also prevents large fluctuations in the olefin to water feed ratios.

Accordingly, it is preferred that the water be injected into a fully operational reactor and, when a loop reactor is used, it is preferred that the materials are circulating at a velocity of at least 0.6 meters/sec when the water is injected. It is also preferred that the water and the olefin are continuously introduced into the reactor at the desired water to olefin ratio.

Any liquid phase catalytic hydrogenation technique may be used to convert aldehydes formed in hydroformylation to alcohols. Many of those employ heterogeneous catalysts, in fixed bed reactors or in slurry circulating reactor systems. They may use any of the conventionally used supported metal catalysts, such as Ni, Pd, or Pt supported on a variety of supports such as granular carbon, silica, silica-alumina, zirconia, silicon carbide, or copper chromite. Other useful catalysts include cobalt compounds; nickel compounds which may contain small amounts of chromium or another promoter; mixtures of copper and nickel and/or chromium; and other Group VIII metal catalysts, such as Pt, Pd, Rh and mixtures thereof, on supports, such as carbon, silica, alumina or silica-alumina. The nickel compounds are generally deposited on support materials such as alumina or kiezelguhr. For example nickel based catalysts may be used such as supported nickel sulphide catalyst. The process may also involve the use of different catalysts in the series of hydrogenation reactors as is described in U.S. Pat. No. 5,324,420. Other suitable catalysts and processes are disclosed in U.S. Pat. No. 4,982,011, U.S. Pat. No. 4,647,707, U.S. Pat. No. 4,658,068, U.S. Pat. No. 5,059,718, U.S. Pat. No. 5,306,848, U.S. Pat. No. 5,324,420, U.S. Pat. No. 5,382,715, U.S. Pat. No. 5,399,793, U.S. Pat. No. 5,663,388, U.S. Pat. No. 5,877,358, which uses intermediate product recycle, or U.S. Pat. No. 6,278,030.

However, we prefer to use a cuprous chrome hydrogenation catalyst and particularly a catalyst containing from about 20% to 40% by weight of each of copper and chromium, based on the weight of the total catalyst including any support, preferably from 25% to 32% of each of copper and chromium, more preferably 29% to 31% of each of copper and chromium. The remainder is typically barium, silica and carbon by way of binders and supports. The catalyst may contain up to 10 wt % silica. Preferred catalysts comprise G-22 RS available from Süd-Chemie and Cu-1155 T available from Engelhard. Cuprous chrome catalysts are preferred because they have a low tendency to cause reaction runaways.

Preferred hydrogenation systems, processes and catalysts are described in PCT Publication WO 2005/058782.

In preparation for the hydrogenation phase the product from hydroformylation is preferably cooled, passed to a decobalting or demetalling and washing unit (though the cooling can also be performed after demetalling depending on what process for demetalling is selected) and filtered to further remove remaining cobalt species. The use of pumice filters is particularly preferred for the removal of cobalt. At this stage the water content of the hydroformylation product is typically between 0.5 and 3 wt % water, which may be dissolved and/or in the form of entrained droplets. Depending on the hydroformylation and/or demetalling process, such water droplets may be very small and be present as a metastable haze that can take 24 hours or more to clear. Typically such a haze represents from 0.1 to 0.4 wt % of free water relative to the organic phase, more typically about 0.2-0.3% wt. These amounts of free water are sufficiently low that after preheating to the desired entry temperature of the hydrogenation reaction, this free water becomes totally dissolved in the organic phase, and no free water enters the hydrogenation reactor itself. If the hydroformylation uses a cobalt catalyst, and the decobalting is using a base, there may also be small amounts of base present in the organic and/or in the free water droplets or haze. The temperature of the product at this stage is typically between 40° C. and 80° C. more typically between 50° C. and 70° C. and especially 60° C. The product is then fed (without any further water addition) to the first hydrogenation reactor where it is hydrogenated over a catalyst bed, preferably a cuprous chrome catalyst at a temperature in the range 170 to 190° C. and a hydrogen pressure of 40 to 60 barg. Alternatively the hydrogenation is performed over a sulphided, alumina supported Co and Mo oxide catalyst at a temperature in the range of 200 to 230° C. and a hydrogen pressure up to 175 barg, or over a sulphided, alumina supported Ni and Mo oxide catalyst at a temperature range of 145 to 185° C. and a hydrogen pressure up to 50 or even as high as 125 barg. The higher pressure is preferred because of suppressing side reaction, an effect that can be noticed up to a pressure of about 125 barg.

The hydrogenation reaction is exothermic and accordingly requires temperature control. Using the cuprous chrome catalyst system, it is preferred that the outlet temperature of the first hydrogenation reactor be no higher than 185° C. since a loss of yield of about 1 to 2% is observed if the temperature exceeds 185° C. The temperature may be controlled by the provision of a cooling jacket around the reactor, in particular if the reactor has a high length/diameter ratio, such as 4 or more. The preferred use of a series of hydrogenation reactors is described in PCT Publication WO 2005/058782.

The product of hydrogenation following the separation of the hydrogen comprises a mixture of the desired alcohols, olefins and paraffins, alcohol dimers, acetals and traces of aldehydes, acids and formates together with dissolved carbon dioxide and monoxide, and dissolved hydrogen and water. The product may then be cooled and purified further, firstly through a coalescer to remove water, followed by fractional distillation to separate the alcohol from the lower boiling fraction of the mixture and a second distillation step, optionally at a different pressure, to separate the alcohol from the higher boiling fraction. Water and any methanol or other lower alcohols typically will be separated with the lower boiling fraction, and may settle out as a separate phase in the tower overhead system, from where they can be discarded or taken for further use.

The alcohols produced in this manner may then be used as raw materials for various reactions including the production of esters.

Esters are most commonly prepared by the reaction of a carboxylic acid and an alcohol accompanied by the elimination of water. Esters may also be formed by reaction of an alcohol with various other reactants including acid anhydrides, acid chlorides, amides, nitrites, ethers, aldehydes, and ketones.

The reaction conditions under which esterification is effected can be varied considerably. Typically the esterification reaction proceeds very slowly at room temperature, but quite rapidly at elevated temperatures. Typically one of the reactants is used in stoichiometric excess in order to drive the reactions. The other reactant is then called the limiting reagent. About 99% of the limiting reagent, e.g., acids, anhydrides, or polyols, can be converted to an ester within a few hours. Limiting reagents are typically reagents which are not present in stoichiometric excess, e.g., limiting reagents used to make plasticisers include diacids and phthalic anhydride.

Because the esterification of an alcohol and an organic acid or anhydride is a reversible reaction, the esterification reaction normally does not go to completion. However, conversions of over 99% can be achieved by removing at least one of the esterification products, typically water. If one of the products is boiling at a lower temperature than the other one and than the reagents, this is typically achieved by distillation. A variety of distillation techniques are known in the art to remove the produced water from the reaction zone. One method of water removal includes carrying out the reaction in a liquid medium which may form an azeotrope having a boiling point that is lower than that of either component of the reaction. If the resulting ester has a boiling point well above 100° C. at atmospheric pressure, then the reaction temperature can be adjusted such that no liquid medium capable of forming an azeotrope is required. Additionally, an entrainer may be used to aid in the distillation of the water from the reaction mixture. Inert materials such as cyclohexane, hexane, benzene, toluene, or xylene may be used as an entrainer in the production of phthalate esters. In addition, the reactant having the lower boiling point may also be employed as the entrainer. In this latter case, the reactant used as the entrainer is typically charged into the reaction mixture in excess over the stoichiometric quantities required for the reaction. Esterification processes, including those employing water removal, may be conducted in a batch or continuous mode of operation. Various esterification processes are disclosed in Volume 9 of the Kirk-Othmer Encyclopaedia of Chemical Technology, Fourth Edition (1994), pp. 762-768, the entirety of which is hereby incorporated by reference.

A conventional batch esterification procedure includes charging all of the reactants into the reactor at the beginning of the reaction cycle. In catalytic esterification processes, the catalyst is typically added to the reaction mixture after the batch reaches a target temperature. The reaction mixture may then be heated further. The temperature of the reaction mixture rises until the boiling point of the reaction mixture is achieved, at which point the entrainer, if used, and water by-product boil out of the reaction mixture. Typically, the overhead vapours are condensed, the water separated from the entrainer, and the entrainer recycled to the reactor vessel.

One conventional process for forming plasticiser esters is disclosed in UK Patent 1,426,057 (Imperial Chemical Industries Limited), wherein plasticiser esters are prepared from phthalic anhydride and a $C_4$ to $C_{14}$ alkanol or mixture of such alkanols. For example, a mixture of phthalic anhydride and one or more of these alkanols may be heated gradually up to 180 to 260° C. in the presence of a titanium catalyst (e.g., titanium isopropoxide). When the temperature reaches 180 to 260° C., the esterification is substantially complete although the residual acidity is about 0.3 to 0.05 mg KOH/gram. Aqueous sodium carbonate solution is then slowly added to the ester product to provide 1 to 12 times the stoichiometric amount of alkali. When the temperature has fallen to between 150 and 200° C., water or a dilute aqueous alkali solution is admitted and the excess alkanol is removed. By this treatment, the titanium catalyst is converted to titanium oxide and precipitated, and, thereafter, may be filtered off with excess sodium carbonate and the residual acidity is reduced to less than 0.05 mg KOH/gram.

Conventional esterification processes may be accomplished in two reaction steps. The first reaction step generally occurs in the absence of an esterification catalyst, while the second reaction step may include the use of an esterification catalyst. In U.S. Pat. No. 5,349,075 to Van den Berg et al. a two step esterification process with a first uncatalysed esterification reaction step conducted at a temperature of at least 200° C., i.e. conditions whereby the more volatile reactant is in the gaseous phase while the less volatile reactant is in the liquid phase, followed by a catalysed second esterification reaction step at a temperature below 100° C. is proposed. The process employs a solid acid catalyst in the second reaction step.

Preferred esterification processes are described in US publication US2006-0270868 and in PCT publication WO 2005/021482.

In the commercial production of plasticiser esters, e.g., phthalates, adipates, and trimellitates, conversions of greater than 99% are desired. The esterification of dibasic acids or acid anhydrides proceeds by the first esterification of one acid group or partial esterification of the anhydride in both instances resulting in the formation of a mono-ester. In this first reaction a catalyst may not be required. Subsequently the esterification is completed to form the di-ester generally in the presence of a catalyst. The catalytic esterification is typically performed by mixing the dibasic acid or anhydride and the alcohol, and raising the temperature to a certain level at which the catalyst is added. Since at least the formation of the mono-ester is a substantially instantaneous reaction a significant amount of esterification therefore occurs before the addition of catalyst, whose presence is desired or even required to drive the reaction to completion in a commercially acceptable time.

The esterification reaction produces water and since the titanium or tin esterification catalysts that are typically used are water sensitive, it is necessary to minimise contact between the water produced in the reaction and the catalyst. Accordingly it has been practice to distill off as much as possible of any water of reaction during the initial phases of the reaction, prior to addition of the catalyst. Thus in a typical reaction such as that described in U.S. Pat. No. 6,355,817 B1, a dialkyl phthalate was produced by reacting phthalic anhydride and an alcohol under reduced pressure to maintain a constant boil up of the reaction mixture. Generally the alcohol is recycled by reflux, which is typically subcooled and can therefore lower the temperature of the reaction mixture and further prolong the reaction cycle time, in particular when heat input capabilities are limited, which is usually the case in an industrial setting.

In our preferred esterification a catalysed batch esterification process is employed wherein an acid or acid anhydride is mixed with an alcohol and the temperature of the mixture is raised to a desired reaction temperature to effect esterification and the water produced in the reaction is vaporised.

The invention is particularly useful in the production of esters useful as plasticisers for the production of plasticised polyvinyl chloride.

Plasticiser esters are typically made by esterification of $C_6$ to $C_{13}$ alcohols with acid or anhydride, the alcohols themselves being made by hydroformylation of the olefins of the present invention. The starting material for the production of di-2-ethyl-hexyl phthalate is generally chemical grade propylene. However, for other alcohols the starting materials are commonly mixtures of olefins. The hydroformylation and hydrogenation reactions are all catalysed. Accordingly, in many of the steps of the processes complex reaction mixtures tend to be formed. The alcohol therefore requires extensive purification to remove unreacted raw materials, undesirable byproducts and catalyst residues.

The plasticiser esters are then produced by reaction of the appropriate purified alcohol with an acid anhydride, frequently phthalic anhydride, trimellitic anhydride, or maleic anhydride, or with an acid. Acids frequently used are adipic acid, trimellitic acid, cyclohexanoic mono- and dibasic acids, benzoic acid, citric acid and the like. The esterification is typically performed using an organo-metallic catalyst, particularly a titanium or tin based catalyst, but many other esterification catalysts like sulphuric acid, methyl sulphonic acid and paratoluene sulfonic acid are also known. After esterification the crude ester will contain contaminants and requires purification.

We have found that the throughput of ester manufacturing facilities may be increased so that larger volumes of product may be produced in the same facility, if the olefin, from which the alcohols used in esterification are produced, is according to the present invention. This is particularly beneficial in the production of plasticiser esters.

As described in PCT publication WO 2005/021482, phthalate esters for use as plasticisers preferably have a light ends content below 600 ppm, more preferably below 500 ppm. It is also independently preferred that the esters have a level of intermediates below 750 ppm, more preferably below 500 ppm. Preferably the esters have a combined light ends and intermediates content below 1000 ppm. All the ppm values expressed above are by weight, and the basis for the ppm wt values given is the total weight of the phthalate ester and the contaminants (light ends and/or intermediates) to which the ppm value relates. The terms "light ends" and "intermediates" are well understood by those skilled in the art, and refer to groups of peaks in the Gas Chromatograph spectrum of a "target ester" that are quite distinct from each other and from the peak(s) corresponding to the target ester itself.

Another important property of the plasticiser is that it has optical clarity, and this can be affected by the presence of impurities which can cause the plasticiser to become hazy over time. We have found that one cause of haze can be the formation of salts of acids present during catalyst neutralisation with alkali. For example, sodium hydrogen phthalate can be formed as a result of the neutralisation of a phthalate ester containing small amounts of phthalic acid with sodium carbonate or bicarbonate or sodium hydroxide, or from the hydrolysis of the monoester or of its salt. In addition, where the olefins of the present invention are feedstocks in the production of plasticiser esters, the antioxidant is selected so that it does not impair the colour of the ester, in particular we prefer to use a phenolic antioxidant having an alkyl group in the 4 position. We prefer to use a phenolic antioxidant composition which comprises low levels of phenolic compounds that have an unsubstituted 4 position. Preferably we use a phenolic antioxidant composition comprising at most 2% by weight each, more preferably 1% by weight each, and most preferably at most 0.5% by weight each of 2,6-dimethyl phenol, 2,6-ditertiarybutyl phenol or 2-methyl-6-tertiarybutyl phenol.

Examples of the alcohol that may be used in the esterification reaction include saturated monohydric aliphatic alcohols such as iso-hexanol, iso-heptanol, iso-octanol, iso-nonyl alcohol, iso-decanol, iso-undecanol, iso-dodecanol and iso-tridecanol. The alcohols may also be used in combination as required. $C_6$ to $C_{13}$ alcohols are preferably employed and the $C_9$ to $C_{11}$ alcohols, especially the $C_{10}$ and $C_{11}$ alcohols are preferred, especially in the production of plasticiser esters that are used in polyvinyl chloride compositions, particularly compositions that are used in electrical applications, such as wire and cable coating.

The esterification reaction preferably employs an organic metal compound catalyst. Examples include an alkyl titanate such as tetra-isopropyl titanate, tetra-n-butyl titanate or tetra-iso-octyl titanate, or an organic tin compound such as tin oxalate, tin octanoate or tin maleate that exhibit a catalytic activity at an esterification reaction temperature.

In one embodiment the esterification reaction is conducted by adding an alcohol derived from the olefins of the present invention to an organic acid or its anhydride, and reacting the mixture, preferably at from 150° C. to 220° C. and preferably for from 1 to 4 hours, in the presence of an organic metal compound catalyst in an inert gas atmosphere while removing water formed. The reaction time is preferably at the lower end of the range, e.g. from 2 to 3 hours, and optimally even less than 2 hours. A base and water, preferably in the form of an aqueous base, is added to the resulting reaction solution to neutralise any unreacted acid and/or mono-ester and to hydrolyse the catalyst. It is also preferred to remove any free water after the crude ester has been treated with the base and before filtration, particularly if the treatment has been with aqueous base. Preferred bases include alkali metal salts, particularly sodium salts, like sodium carbonate, and alkali metal hydroxides, like sodium hydroxide, e.g. aqueous sodium hydroxide. Any excess alcohol is recovered typically by stripping (which advantageously removes alcohol, water and other light materials) and the resulting ester product is then purified to obtain the final ester.

The present invention is illustrated by the following Examples.

Example 1

A stirred tank reactor was filled with (at 150° C.) 26.2 m3 of a preheated $C_{10}$ alcohol derived from a branched nonene containing 10 ppm Annulex BX antioxidant, 6.2 m3 recycle $C_{10}$ alcohol with a purity of 80% by weight and 9.9 tons of phthalic anhydride. Annulex BX, obtained from Hodgson Chemicals Limited (now Clariant Life Science Molecules (UK) Ltd.), comprises approx. 56 wt % 2,4-dimethyl-6-tertiary butyl phenol, 18 wt % butylated hydroxytoluene and 15 wt % 2,5-dimethyl-4-tertiary butyl phenol.

The reactor contents were heated with high pressure steam and when the temperature reached 180° C., 42 liters of tetra-iso-octyl titanate were injected into the reaction mixture followed by continued heating to 220° C., the reaction temperature. At 215° C. the pressure in the reactor was gradually reduced from atmospheric pressure (100 kPa) to 30 kPa with the objective to ensure continuous alcohol reflux at constant reaction temperature 220° C. After 119 minutes from the start of filling the reactor a monoester conversion of 99.96% was obtained. The total cycle time from the start of the batch to a fully emptied reactor was 131 minutes.

Comparative Example 2

Example 1 was repeated except that a $C_{10}$ alcohol containing 100 ppm of the Annulex BX antioxidant was used. After 132 minutes from start of filling the reactor a monoester conversion of 99.96% was obtained. The total cycle time from the start of the batch to a fully emptied reactor was 144 minutes.

Comparison of the examples shows the reduction in reaction cycle time that may be accomplished when using alcohols obtained from the olefin composition of the present invention.

The invention claimed is:

1. An olefin composition comprising a branched chain olefin having from 5 to 13 carbon atoms and containing from 5 to less than 50 ppm by weight of an antioxidant, based on the weight of olefin.

2. The composition according to claim 1 wherein the branched chain olefin comprises nonenes.

3. The composition according to claim 1 wherein the branched chain olefin comprises dodecenes.

4. The composition according to claim 1 wherein the branched chain olefin comprises octenes.

5. The composition according to claim 1 in which the branched chain olefin is obtained by the oligomerisation of one or more $C_2$ to $C_6$ olefins.

6. The composition according to claim 5 in which the branched chain olefin is obtained by the oligomerisation of one or more $C_3$ to $C_5$ olefins.

7. The composition according to claim 5 in which the oligomerisation is performed using a solid phosphoric acid catalyst.

8. The composition according to claim 5 in which the oligomerisation is performed using a zeolite catalyst.

9. The composition according to claim 5 in which the oligomerisation is performed using a nickel containing catalyst.

10. The composition according to claim 1 containing from 10 to 40 ppm by weight of the antioxidant.

11. The composition according to claim 10 containing from 20 to 30 ppm by weight of the antioxidant.

12. The composition according to claim 1 in which the antioxidant is a phenolic antioxidant.

13. The composition according to claim 12 in which the phenolic antioxidant has an alkyl group in the 4 position of the phenol moiety.

14. The composition according to claim 12 in which the phenolic antioxidant contains a tertiary alkyl group in the 2 and/or the 6 position of the phenol moiety.

15. The composition according to claim 14 in which the tertiary alkyl group is tertiary butyl.

16. The composition according to claim 12 in which the antioxidant comprises 2,4-dialkyl-6-tertiarybutyl phenol.

17. The composition according to claim 16 in which the antioxidant comprises 2,4-dimethyl-6-tertiarybutyl phenol.

18. The composition according to claim 12 in which the antioxidant comprises 2,6-ditertiarybutyl-4-alkyl phenol.

19. The composition according to claim 18 in which the antioxidant comprises 2,6-ditertiarybutyl-4-methyl phenol.

20. The composition according to claim 12 in which the phenolic antioxidant comprises at most 2% by weight of phenolic compounds having no substitution at the 4 position of the phenol moeity.

21. A process for the production of an olefin composition according to claim 1, which process comprises
   i) oligomerising one or more $C_2$ to $C_6$ olefins to produce a $C_5$ to $C_{13}$ branched chain olefin oligomer
   ii) separating an olefin oligomer material comprising $C_5$ to $C_{13}$ branched chain olefin oligomer from the product of the oligomerisation reaction
   iii) passing the olefin oligomer material to a storage and/or transportation vessel
   iv) providing 5 to less than 50 ppm by weight of an antioxidant to the olefin oligomer material between the separation and the storage and/or transportation vessel, to form the desired olefin composition.

22. The process according to claim 21 in which the antioxidant is provided as a liquid.

23. The process according to claim 22 in which the antioxidant is injected into the olefin oligomer material by means of an injection pump.

24. The process according to claim 23 in which the amount of antioxidant that is injected is controlled by on line analysis of the olefin oligomer material and adjusting the amount of antioxidant injected by the pump according to the results of the on line analysis.

25. The process according to claim 21 in which the olefin oligomer material separated from the product of the oligomerisation reaction is separated into different $C_5$ to $C_{13}$ branched chain olefin-containing streams and the antioxidant is provided separately to at least two of the different streams.

26. The process according to claim 21 in which a corrosion inhibitor and/or an antifoulant is provided in the olefin oligomer material prior to or during the separation step.

27. In a process for hydroformylation, the improvement comprising contacting a feedstock comprising the composition of claim 1 with a hydroformylation catalyst.

28. The process according to claim 27 in which said hydroformylation catalyst comprises cobalt.

29. The process according to claim 27 in which said hydroformylation catalyst comprises rhodium.

30. The process of claim 27 including a step comprising hydrogenation to obtain at least one $C_6$ to $C_{14}$ alcohol.

31. The process of claim 30 wherein said at least one $C_6$ to $C_{14}$ alcohol is esterified.

32. The process according to claim 31 wherein said at least one alcohol is esterified with a polycarboxylic acid or anhydride.

33. The process according to claim 32 in which the polycarboxylic acid or anhydride is phthalic acid or anhydride, cyclohexane dicarboxylic acid, adipic acid or trimellitic acid or anhydride.

34. The process according to claim 33, wherein said hydroformylation catalyst comprises at least one metal selected from cobalt and rhodium, and wherein said at least one alcohol includes at least one $C_9$ to $C_{11}$ alcohol.

* * * * *